(12) United States Patent
Statham

(10) Patent No.: US 9,470,705 B2
(45) Date of Patent: Oct. 18, 2016

(54) METHOD AND SYSTEM FOR DETERMINING THE WALKING OR RUNNING SPEED OF A PERSON

(75) Inventor: Andrew Statham, Delft (NL)

(73) Assignee: Nederlandse Organisatie voor toegepast-natuurwetenschappelijk Onderzoek TNO, Delft (NL)

( * ) Notice: Subject to any disclaimer, the term of this patent is extended or adjusted under 35 U.S.C. 154(b) by 870 days.

(21) Appl. No.: 13/818,019

(22) PCT Filed: Aug. 26, 2011

(86) PCT No.: PCT/NL2011/050582
§ 371 (c)(1),
(2), (4) Date: Apr. 30, 2013

(87) PCT Pub. No.: WO2012/026818
PCT Pub. Date: Mar. 1, 2012

(65) Prior Publication Data
US 2013/0211775 A1    Aug. 15, 2013

(30) Foreign Application Priority Data

Aug. 26, 2010 (EP) .................................... 10174145

(51) Int. Cl.
*G01P 11/00* (2006.01)
*G01P 3/00* (2006.01)
(Continued)

(52) U.S. Cl.
CPC .............. *G01P 3/00* (2013.01); *A43B 7/1455* (2013.01); *A61B 5/1038* (2013.01); *A61B 5/112* (2013.01);
(Continued)

(58) Field of Classification Search
CPC .......... G06K 9/00348; A63B 2220/30; A63B 2220/56; A63B 2220/836; A63B 2225/50; A63B 24/0062; A63B 69/0028; G01P 3/00; G01C 22/006
See application file for complete search history.

(56) References Cited

U.S. PATENT DOCUMENTS

| 4,578,769 A | 3/1986 | Frederick |
| 5,720,200 A | 2/1998 | Anderson |

(Continued)

FOREIGN PATENT DOCUMENTS

| CN | 1329713 A | 1/2002 |
| EP | 0119009 | 9/1984 |

(Continued)

OTHER PUBLICATIONS

Japanese Office Action from Application No. 2013-525856 dated Jun. 16, 2015 with English translation.

(Continued)

*Primary Examiner* — Elias Desta
(74) *Attorney, Agent, or Firm* — Swanson & Bratschun, L.L.C.

(57) ABSTRACT

Method and system for determining the speed of a walking or running person from a foot motion. The method comprises providing (1) a pressure sensor between the foot and the ground, which sensor may be placed on or in an insole of a shoe. The pressure sensor is configured for transmitting pressure data to a communication unit (9). The method further comprises a step of determining a center of pressure gait line (3) and calculating the center of pressure speed (4) from the gait line. In addition, the method comprises the step of detecting whether the person is walking or running (5). Another step (6) is obtaining a correlation between the speed of a person and the center of pressure speed. As a final step (7) of the method the speed of the person is deduced from the correlation. The system comprises a human interface for control and to inform the user.

17 Claims, 7 Drawing Sheets

(51) Int. Cl.
| | | |
|---|---|---|
| *A43B 7/14* | (2006.01) | |
| *A61B 5/103* | (2006.01) | |
| *A61B 5/00* | (2006.01) | |
| *A63B 24/00* | (2006.01) | |
| *A63B 69/00* | (2006.01) | |
| *A63B 71/06* | (2006.01) | |
| *A61B 5/11* | (2006.01) | |
| *G06K 9/00* | (2006.01) | |

(52) U.S. Cl.
CPC ........... *A61B 5/1123* (2013.01); *A61B 5/6807* (2013.01); *A63B 24/0062* (2013.01); *A63B 69/0028* (2013.01); *A63B 71/0622* (2013.01); *A63B 2024/0071* (2013.01); *A63B 2071/063* (2013.01); *A63B 2220/17* (2013.01); *A63B 2220/30* (2013.01); *A63B 2220/56* (2013.01); *A63B 2220/836* (2013.01); *A63B 2225/50* (2013.01); *G06K 9/00348* (2013.01)

(56) References Cited

U.S. PATENT DOCUMENTS

| | | | |
|---|---|---|---|
| 6,360,597 | B1 | 3/2002 | Hubbard |
| 6,826,477 | B2 * | 11/2004 | Ladetto .................. G01C 21/16 340/944 |
| 6,836,744 | B1 | 12/2004 | Asphahani |
| 2002/0040601 | A1 | 4/2002 | Fyfe et al. |
| 2007/0275830 | A1 | 11/2007 | Lee |

FOREIGN PATENT DOCUMENTS

| | | |
|---|---|---|
| JP | S59-171564 | 9/1984 |
| JP | H6-14803 | 1/1994 |
| JP | H10-5194 | 1/1998 |
| JP | 11-113884 | 4/1999 |
| JP | 2007-300951 | 11/2007 |
| SU | 1326296 | 7/1987 |
| WO | WO 00/25090 | 4/2000 |
| WO | WO 2008/039082 | 4/2008 |

OTHER PUBLICATIONS

Grundy, et al. (1975) Journal of Bone and Joint Surgery 57(1):98-103, "An investigation of the centers of pressure under the foot while walking".

International Search Report from PCT/NL2011/050582, dated Nov. 29, 2011.

Sempler, et al. (2008) Clinical Biomechanics 23(5):689-690, "Influence of walking speed on the duration and velocity of the centre of pressure in patient with rheumatoid arthritis".

Verkerke, et al. (2005) Journal of Biomechanics 38:1881-1885, "Determining the centre of pressure during walking and running using an instrumented treadmill".

Chesnin, et al. (2000) Gait and Posture 12:128-133 "Comparison of an in-shoe pressure measurement device to a force plate: concurrent validity of center of pressure measurements".

Hsue, et al. (2009) Gait and Posture 29:471-476 The dynamic balance of the children with cerebral palsy and typical developing during gait. Part II: Instantaneous velocity and acceleration of COM and COP and their relationship.

Arendse, et al. (2004) Medicine & Science in Sports & Exercise 36(2):272-277, "Reduced Eccentric Loading of the Knee with the Pose Running Method".

Couillandre and Breniere (2003) Journal of Motor Behaviour 35(3):221-227, "How Does the Heel-Off Posture Modify Gait Initiation Parameter Programming?".

De Wit, et al. (2000) Journal of Biomechanics 33:269-278, "Biomechanical Analysis of the Stance Phase During Barefoot and Shod Running".

Hasegawa, et al. (2007) Journal of Strength and Conditioning Research 21(3):888-893, "Foot Strike Patterns of Runners at the 15-km Point During an Elite-Level Half Marathon".

Hennig and Milani (1995) Journal of Applied Biomechanics 11(3):299-310, "In-Shoe Pressure Distribution for Running in Various Types of Footwear".

Larson, et al. (2011) Journal of Sports Sciences 29(15):1665-1673, "Foot Strike Patterns of recreational and Sub-Elite Runners in a Long-Distance Road Race".

Nielsen (2000) Department UW-la Crosse JUR, 3(1):301-304 "The Relationship between Plantar Loading and Rearfoot Motion during Walking" (Kristine Nielsen, Physical Therapy Department).

* cited by examiner

METHOD AND SYSTEM FOR DETERMINING THE WALKING OR RUNNING SPEED OF A PERSON

RELATED APPLICATIONS

This application is a 35 U.S.C. §371 national phase application of PCT/NL2011/050582 (WO 2012/026818), filed on Aug. 26, 2011, entitled "Method and System for Determining the Walking or Running Speed of a Person", which application priority to European Application No. 10174145.2, filed Aug. 26, 2010, which is incorporated herein by reference in its entirety.

FIELD OF THE INVENTION

The present invention relates to a method for determining the speed of a walking or running person from foot motion. The present invention also relates to a system for providing the speed of a walking or running person.

BACKGROUND

Measuring the walking or running speed of a person is of importance for science, therapy and training. Information obtained by such a measurement can be used to improve human performance, for example in sports and rehabilitation.

A number of technologies exist that allow measurement of running speed, these include the use of GPS (global position system), accelerometer inertia devices, accelerometer based pedometers and timing/counting sensors. Each of these methods has varying degrees of accuracy and each has its limitations. General timing and counting devices do not offer a very reliable measurement of speed or distance since they rely upon the assumption that the stride length of a person remains constant irrespective of speed and environment. From the location as determined by GPS the speed can be derived in a straightforward way by measuring the elapsed time. However, GPS based speed measurement requires that the sensor is always in view of a number of satellites. Therefore it is often not possible to measure the speed in high rise urban areas, heavily wooded or mountainous areas, inside buildings like indoor sport buildings or in tunnels and subways.

For training and therapy one is often not only interested in speed but also in other parameters characterising the walking or running behaviour of the person. Typically one may be interested in biomechanical parameters like foot strike location, speed of pronation, contact time, and heel off speed. These parameters cannot be obtained with a GPS system because GPS only provides information about the location of the person. So, to obtain the biomechanical parameters additional sensors have to be used. Such additional sensors make the system expensive and complex.

U.S. Pat. No. 6,360,597 discloses a system for determining the gait line of a walking person. A gait line is a line that illustrates how the average pressure, or better the centre of pressure, of a foot changes during the time that the foot is in contact with the ground. This known system comprises force-sensing sensors that are inserted into a shoe. The spatially averaged output signal of the sensors provides a gait line in a two dimensional space. In addition, this patent publication discloses a method to distinguish different phases of the foot contact with the floor. In particular this known method allows determining the duration of heel strike, toe-off, and mid-stance. So, this known method provides a limited number of basic parameters concerning the contact time of the different parts of a foot with the floor.

U.S. Pat. No. 4,578,769 discloses a method for determining the speed of a person while running. This known method comprises the use of a sensor that is located in the sole of a shoe for determining whether or not the foot is in contact with the ground. The time during which the foot is in contact with the ground is used to determine the running speed of the person. For each particular runner a linear relationship between the contact time and the running speed, which relationship is different for each person, is determined empirically. This relationship is stored in a microprocessor and is used to calculate the running speed.

However, contact time depends on factors other than running speed alone. Therefore this approach has a limited accuracy.

US patent application 2002/0040601 discloses a motion analysis system comprising accelerometers and a tilt sensor that are mounted on a shoe. The average horizontal speed of the shoe as determined from the accelerations measurements and analysis corresponds to the speed of the person. In addition also parameters like the stride length, the height of the foot off the ground, and the degree of pronation can be derived from the measurements.

A problem that one encounters when using accelerometers for deriving the walking or running speed from the foot motion of a person is that this method can become less accurate if the accelerometers are mounted incorrectly or if they become disorientated during use. If the foot is swung through in an unusual orientation the accuracy of the model can be additionally compromised. Unusual dynamic movements during the foot swing can also disrupt the measurement. Another problem of a method using an accelerometer is that additional sensors of another type have to be applied to derive parameters which require information about the gait line.

SUMMARY

It is an objective to provide a method for determining the speed of a walking or running person from foot motion, which method is not expensive and which method can easily be combined with or incorporated into methods for determining biomechanical parameters of a walking or running person.

A method is provided wherein the speed of a walking or running person is derived from foot motion, which method is characterised by the steps of
  providing a least one pressure sensor between a first foot of the person and a support surface so as to determine the centre of pressure, the pressure sensor being configured for transmitting pressure data to a communication unit, followed by
  determining a centre of pressure gait line and calculating a centre of pressure speed from the gait line, and
  detecting whether the person is walking or running,
  obtaining a correlation between the speed of a walking or running person and the centre of pressure speed,
followed by
  deducing the speed of the person from the correlation.

The speed of a person is the velocity at which the centre of mass of a person moves. This speed has to be distinguished from the velocity of for example a single hand or any other limb. More in particular it has to be distinguished from the velocity of a foot.

An advantage of using a pressure sensor for determining the speed of the person is, that pressure sensors are commonly available at reasonable prices, are light and thin, can easily be incorporated in for example a shoe or insole, and that the signal processing is not complex. Pressure sensors are often used to determine the biomechanical parameters of a human, for example for, but not limited to rehabilitation and laboratory analysis.

The above mentioned objective is obtained with this advantage because no specific and complex equipment is needed. In particular this method can be implemented with systems that are in use for determining biomechanical parameters. Therefore the method provides a low cost method to determine the speed of a person. Further, the pressure sensor provides a gait line that can be used for analysing the way of walking or running.

Another objective is to provide a system for providing the speed of a walking or running person, which system automatically detects whether the person is walking or running and which system nevertheless is not expensive and can easily be used by the walking or running person.

A system for providing the speed of a walking or running person is provided, comprising a sensor for sensing whether a first foot of the person is in contact with a supporting surface and characterised in that the system further comprises a pressure sensor for determining the centre of pressure of the second foot, which sensor is suitable for placing in a shoe, (or between a foot and the running surface, whether that be in a shoe or on/in the surface or anywhere in between)

a memory for storing the correlation between the speed of a walking or running person and the centre of pressure speed, a processing unit for calculating a centre of pressure speed, a human interface for presenting the speed.

An advantage of using two sensors, one at each foot, is that automatic detection of whether the person is walking or running is possible. The difference between walking and running is that at running the two feet are lifted off from the ground simultaneously during some time, while during walking always one of the feet is in contact with the ground. The advantage of using a memory for storing a correlation between centre of mass speed and the centre of pressure speed is that the centre of mass speed can automatically be derived from the calculated centre of pressure speed without interference by the person.

The above mentioned objective is obtained with these advantages because no specific and complex equipment is needed and the person need not worry about the data analysis. More in particular the person will be informed in a clear way about his speed, for example in real time during running if desired.

BRIEF DESCRIPTION OF THE FIGURES

These and other aspects will become apparent from a description of exemplary embodiments with reference to the following figures.

DETAILED DESCRIPTION OF EXEMPLARY EMBODIMENTS

Figure 1A:
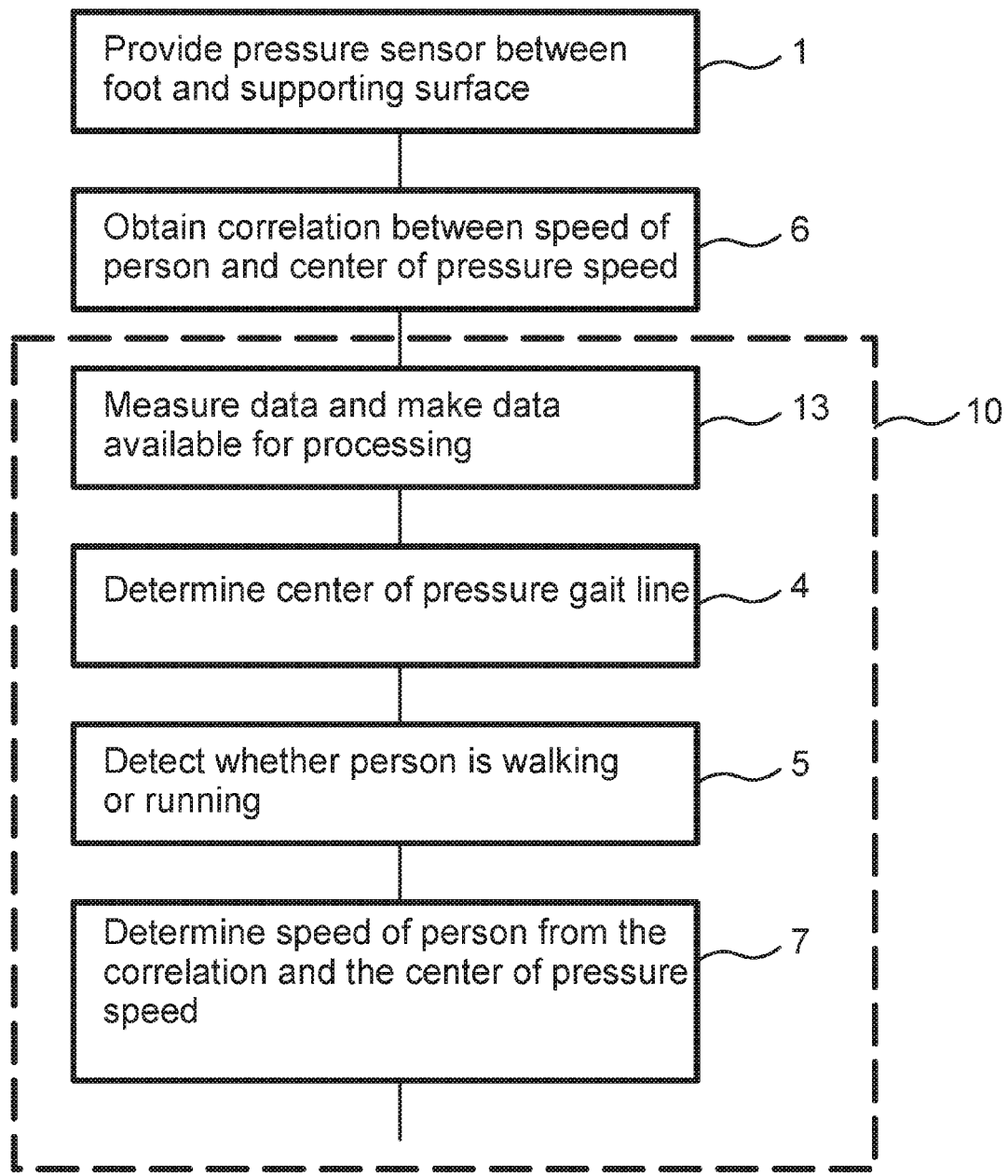
FIG. 1a shows a flow chart of a method of deriving the speed of a walking or running person.

FIG. 1a shows a flow chart of a method of deriving the speed of a walking or running person. The method comprises a first step 1 wherein a pressure sensor is provided between the foot and a supporting surface like a floor or a road on which the person is walking or running. In a second step 6 a correlation between the speed of a person and the centre of pressure speed is obtained. This step could be performed at a later stage. In a third step 13 the pressure sensor measures data and this data is made available for processing. In a fourth step 4 a centre of pressure gait line is determined and from this the centre of pressure speed $v_{COP}$ is calculated. In a fifth step 5 it is detected whether the person is walking or running. This step may be performed at the time that the centre of pressure gait line is determined. In a sixth step 7, the speed of the person is deduced from the correlation and the centre of pressure speed. As will be appreciated, first and second steps 1, 6 may be executed once, before an instance where the person starts walking or running, only the third to sixth steps 13, 4, 5, 7 shown in dashed box 10 being executed during the instance when a person is actually walking or running, or afterwards. The steps of dashed box 10 may be executed repeatedly, to perform determinations of the speed for different time points or time intervals.

Figure 1B:
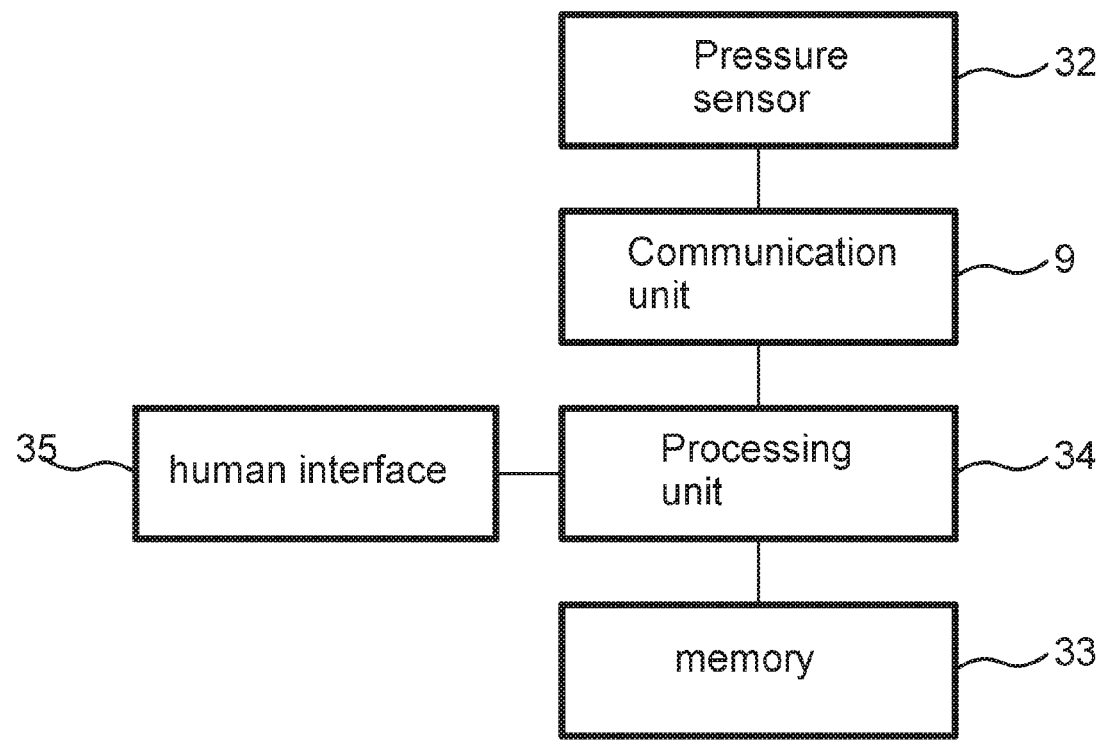
FIG. 1b shows a system for deriving the speed of a walking or running person.

FIG. 1b shows a system (30) for determining the speed of a walking or running person. The system comprises one or more pressure sensors (32) (shown as one box), a communication unit 9, a memory 33, a processing unit 34 and a human interface 35. Pressure sensor or sensors 32 are coupled to processing unit 34 by communication unit 9. Furthermore, processing unit (e.g. a programmed computer) 34 is coupled to memory 33 and human interface (e.g. a display device) 35.

Figure 1C:
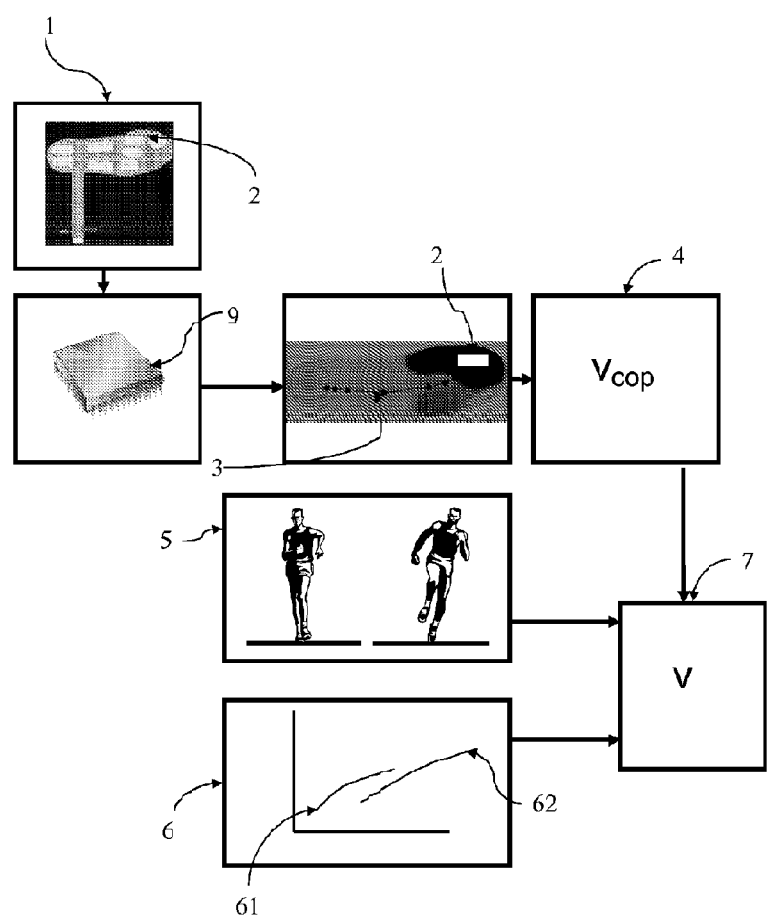
FIG. 1c illustrates a method of deriving the speed of a walking or running person.

Different steps of a method of deriving the speed of a walking or running person from foot motion are illustrated more graphically on the basis of the embodiment as shown in FIG. 1c. One of the steps of the method is a step (1) of providing a pressure sensor between the foot and a supporting surface like a floor or a road on which the person is walking or running. The pressure sensor is suitable for measuring the pressure at different locations (2) of the foot. A communication unit (9) makes the data from the pressure sensor available for determining a centre of pressure gait line (3) from which the centre of pressure speed $V_{COP}$ is calculated (4). Another step (5) is detecting whether the person is walking or running. This step has to be performed after the pressure sensor is placed and may be performed at the time that the centre of pressure gait line is determined. However, this step (5) can also be performed later (post-processing), but should be performed before the final step (7) of deducing the speed of the person. Still another step (6) is obtaining a correlation between the speed of a person and the centre of pressure speed. This step may actually be performed before the person starts walking or running. However, this step may also be performed afterwards (post-processing) but in any case before the final step (7) of deducing the speed of the person from the correlation, which final step has to be performed after the other steps of the method.

Figure 3:
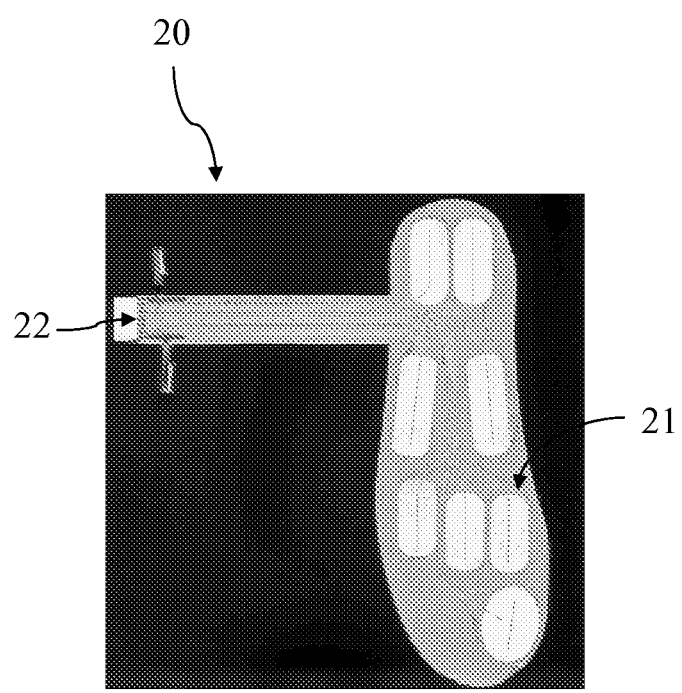
FIG. 3 shows an exemplary geometry of a pressure sensor for determining the centre of pressure.

The pressure of the foot at different locations is measured by pressure sensors situated between the foot and the surface supporting the person such that the person's weight will actuate a pressure sensor. If in this document reference is made to the plural sensors it has to be understood that they need not to be physically separate devices. It may also be one sensor that allows measuring the pressure at different locations, for example a sheet of piezo-electric material with a matrix electrode. Preferably the sensors are fixed in or on an insole that is placed in a shoe. An example of such an insole is shown in FIG. 3. This particular example of an insole (20) comprises eight pressure sensors (21) and a connector (22) to send the output signal of the sensors to a communication or processing unit.

Although it is preferred that the sensors are fixed in or on an insole that is placed in a shoe, the sensors may for example also be attached to or placed in the shoe sole or glued to the foot sole. The sensors may even be mounted in or on the floor or any other convenient surface or interface between the foot and the surface on which the person is standing, walking, or running. Evident disadvantages of sensors on the floor are that the speed of the person can only be determined at a very specific location, for example at a training centre, and that the number of sensors must be very high or the area very large. Examples of sensors that are suitable for measuring the pressure of the foot on the supporting surface are sensors based on electrical properties like capacitance (e.g. carbon laminate), inductance, or piezo-electric or piezo-resistance effect. However, also sensors based on optical properties, like reflectance or diffraction (e.g. Doppler shift, Bragg optical fibres) or colour change (e.g. piezo-optic) are suitable.

The output signal of the sensors is sent to a communication unit (9), which communication unit is suitable for providing the data for further analysis and processing in order to determine the speed of the person, either in real-time or later. The data comprise for each sensor or for each location on a sensor the pressure and the time at which that pressure is measured. The communication unit may store the sensor data or send the data by wire or wirelessly to a processing unit suitable for automatic processing of the data. The processing unit and the communication unit may be incorporated within a single device. The communication unit may also be suitable for receiving signals, for example a signal for switching the sensor on and off. Switching off the sensor might be advantageous for saving energy of a battery during times where there is no need for measuring the speed. The processing unit may be attached to the person, for example by using a belt or armband, or may be at a remote location. In the latter situation a wireless communication between the communication unit and the processing unit is preferred to minimize the hindrance for the person when the sensors are attached to the person, for example in an insole. Although it is preferred to process the data automatically, allowing for example to provide real-time information about the speed, it is recognised that it is also possible to perform the processing of the sensor data by hand. If the data are analysed by hand, the communication unit may for example be a memory suitable for storing the sensor data, which memory can be read out later.

In an embodiment in which the pressure sensors are attached to the floor, the communication between the communication unit and processing unit may be by wire, for example a glass or copper fibre, if the processing unit is at a fixed location. If, however, the person is carrying the processing unit, then wireless communication is preferred.

A method according to which the person is carrying the processing unit will be advantageous for providing the person in real-time with information about the speed, for example optically, using a display or signal lamps, or acoustically, using a recorded voice or a signal sound.

In the preferred embodiment in which a processing unit is used for processing the data, the processing unit is configured for calculating a gait line and the centre of pressure speed based on the output signal of the pressure sensors. As mentioned before, it is also possible to do the calculation, or a part of the calculations, by hand. The pressure at different locations of the foot is measured with a sampling frequency that is considerably higher than the frequency with which the foot strikes the ground during walking or running. This high sampling frequency allows a semi-continuous measurement of the centre of pressure (COP) position. The COP position at a given moment in time is the point where the resultant of all ground reaction forces acts at that moment. This COP position varies in time along a foot during walking or running and results in what is commonly known as the gait line. The COP is calculated by weighting each pressure measurement by its magnitude and position so as to be able to resolve all forces into one point. More in particular, the COP (x) in a direction x may be calculated using the formula:

$$COP(x) = \frac{\sum_i x_i \cdot F_i}{\sum_i F_i}$$

where $F_i$ is a pressure at a distance $x_i$ from a reference point in the x-direction. The summation is over discrete measuring positions i of the sensor. It has to be understood that the gait line need not to be a line connecting points in space. The word gait line is used to describe the spatial distribution of the different centres of pressure during the contact time of the foot with the supporting surface.

When sequential COP positions are connected by a line in a two-dimensional representation, a gait line (3) is obtained as is shown in FIG. 1. The COP speed is defined as the speed at which the centre of pressure moves. It can easily be derived from the distance between two centres of pressure and the elapsed time. For the purpose of determining the speed of a person it is observed that preferably the COP velocity is calculated on the basis of a starting point that is related to the point when and where the foot strikes the floor first and an end point that is related to the point when and where the foot lifts off the floor. In practice, the COP may move backward (in relation to the body's direction of motion) for a short time during landing of the foot. Therefore, the moment and location at which the COP moves in the forward direction of the foot from the first strike, can be defined as the start time and location, respectively. The end time and end location can be determined in a similar way, viz. the time and location at which the COP does not move anymore in a forward direction, for instance due to the fact that the foot is lifted from the floor, is static or moves a little back. The COP velocity can be defined as the quotient of the distance between the start point and the end point and the elapsed time between these points.

In an embodiment, determination of the COP velocity comprises steps of determining the start time and the end time. In a first step of this embodiment processing unit 34 determines the CPO position as a function of time (for example for a series of time points). In a second step processing unit 34 determines a start time, at which the COP starts moving in the forward direction of the foot from the first strike In a third step processing unit 34 determines an end time after which the COP does not move anymore in the forward direction. In a fourth step processing unit 34 computes the COP velocity from a quotient of the distance between the COP positions at the end time and the start time and the elapsed time between the start time and the end time. Instead of computing the quotient, processing unit 34 may compute the coefficients of a fitted linear relationship between COP position and time, which fits the computed COP position as a function of time. Fitting techniques are known per se. The use of such start and end times improves the accuracy of the correlation between COP velocity and walking or running speed. It may remove dependence on running style etc. In each case, processing unit 34 then uses the correlation to determine the speed of running or walking from the computed COP velocity.

It may be noted that over much of the time interval between the start time and the end time the COP position changes substantially linearly as a function of time in many cases. Hence, processing unit 34 may obtain a similar COP velocity from the quotient of the distance between the COP positions at any first and second time in this time interval and the elapsed time between the first and second time interval. In an embodiment, processing unit 34 selects a first time point at which the instantaneous COP speed in the forward direction starts to exceed a threshold value that is larger than zero. The instantaneous COP speed may be determined from the change of COP positions between successive sampling time points, or a fit of a linear relationship between COP position as a function of time at the time point for which the instantaneous speed is determined. The threshold may be selected so as to exclude a stage after first contact at which the COP speed is substantially smaller than (e.g. less than half of) average COP velocity. A fixed threshold may be used for example, or the threshold may be derived from observed average of peak COP velocity. The use of such a first time point improves the accuracy of the correlation between COP velocity and walking or running speed. It may remove dependence on running style etc.

Furthermore, processing unit 34 may select a second time point at which the instantaneous COP speed ceases to exceed a further threshold value grater than zero (which may be the same as the threshold used to obtain the first time point). As may be noted the method wherein a start and endpoint corresponding to the start and end point of forward motion are used corresponds to use of a threshold of zero. Processing unit 34 may compute the COP velocity from a quotient of the distance between the COP positions at the first and second time points and the elapsed time between the first and second time points, or from a coefficient of a fitted relationship.

The invention, among others, provides the insight that the correlation between the speed of a human and the centre of pressure speed is mainly determined by whether the human is walking or running. The inventors have, surprisingly, found that the relation between the centre of mass speed and the centre of pressure speed is to a large extent consistent for either running or walking, but that this relationship is different for walking and running. In other words, there is a general relationship between the speed of a running person and the centre of pressure speed. There is also a general relationship between the speed of a walking person and the centre of pressure speed, but this relationship may be different from the relationship for a running person. Because of the general relationships it is possible to use a generally applicable master curve for the correlation between the walking or running speed and the COP speed if one knows whether the person is walking or running. The correlation or the master curve for the correlation represents the relationship between the centre of mass speed and the centre of pressure speed, or at least an average of the relationship. One has to realise that the speed itself cannot sufficiently discriminate between running and walking, because within a certain range of speeds, for example in the range of 4 to 10 km/h, a person might be either running or walking.

In an advantageous embodiment of the method the master curve comprises both data for walking and for running. However, if it is decided on beforehand that a person will only run or if one is only interested in the running speed, the master curve for walking can be omitted. For determining the running speed, it only has to be detected whether the person is running or walking. The speed will only be calculated for the time the person is or was running. The same holds mutatis mutandis for walking.

The correlation between the speed of a human and the centre of pressure speed is in particular very good (i.e. produces very little inaccuracy) for a person during a training session but it is also good for one and the same person during different training sessions. The inventors even observed (see FIG. 4) that it is possible to obtain a master curve of this correlation for different persons with a reasonable degree of accuracy. This observation allows that such a master curve, when it has been established once, can be used in many situations without the need to determine the correlation between the centre of mass speed of the human and the centre of pressure speed for each specific person, application, or situation. This master curve may be a linear relationship between the speed of the person and the COP speed, a polynomial of a higher order, or any other type of relationship, such as a relationship defined by a table of corresponding centre of mass speeds and centre of pressure speeds.

If one is only interested in the speed of a running person, the master curve may contain only the correlation between the COP speed and the running speed. If, on the other hand, one is only interested in the speed of a walking person, the master curve may contain only the correlation between the COP speed and the walking speed. Preferably, however, the master curve will contain the correlation for both walking and running. In this case the curve may typically have two parts, one for walking (61) and one for running (62) as is shown in FIG. 1. Although the word "curve" is used here, one will appreciate that the way in which the correlation is stored is not limited to a graphical representation. Coefficients of a linear relationship between the speed of the person and the COP speed may be stored to represent the master curve, coefficients of a polynomial of a higher order that represents the relationship may be stored, or table of corresponding centre of mass speed values and centre of pressure speed values may be stored for example. Preferably, the master curve is stored in a data storage medium that allows for further processing easy access to the data relating the COP speed and the speed of the person. This storage medium preferably is comprised in the processing unit.

Figure 2:
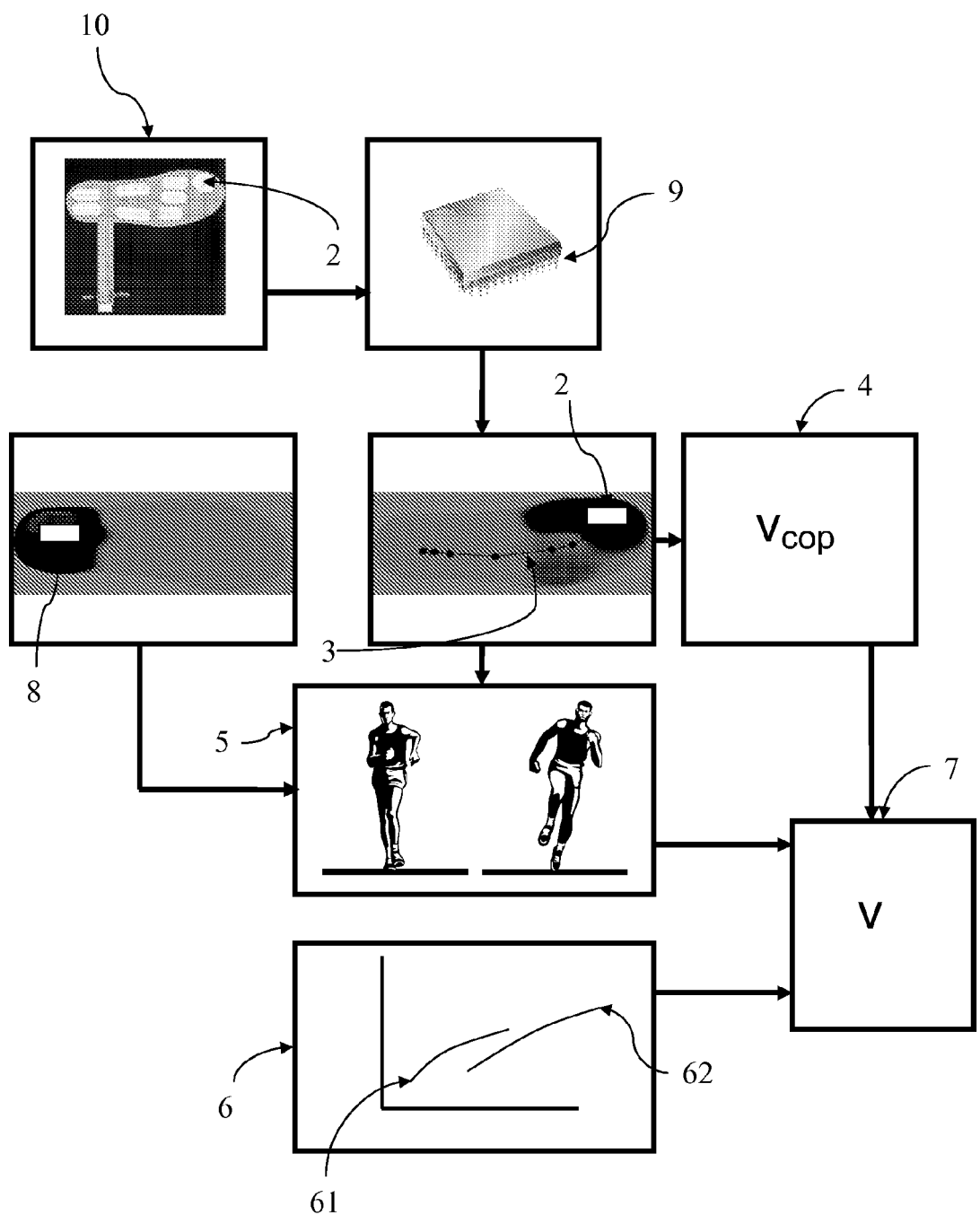
FIG. 2 illustrates another embodiment of such a method.

The difference between walking and running is that during walking always one of the feet is on the ground, whereas during running there is a certain time interval during which both feet are lifted from the ground. So, it can easily be observed by the person himself or by an accompanying person, like for example a trainer, whether the person is walking or running. This information can be used to select the proper correlation curve, viz. the curve for a walking person or the curve for a running person. However, the preferred way to determine whether the person is walking or running is automatic as is shown in FIG. 2. In one embodiment pressure sensors (10) for determining the centre of pressure are situated under both feet. Indeed, from the output signal of the sensors it can be determined whether or not the feet are lifted from the ground. When always at least one of the feet is on the ground walking is detected, whereas running is detected when there time interval are detected during which both feet are lifted from the ground. A further advantage of using pressure sensors under both feet might be increased accuracy.

In another embodiment, shown in FIG. 2, only for one of the feet such pressure sensors (2) are used, whereas for the other foot a different type of sensor (8) is used to determine whether or not the foot is in contact with the ground at a certain moment. This different type of sensor may be for example be a very simple pressure sensor, synchronised with the sensor for the first foot. However, it may also be a same type of sensor as the first sensor but only used in a mode to detect contact with the floor. Whatever additional sensor is used for the second foot, such an embodiment of the method allows that the proper correlation curve (61,62) for determining the speed (7) is selected automatically.

A correlation between the speed of a walking or running person and a centre of pressure velocity, such as the master curve, can be obtained determining centre of pressure velocity during walking or running and measuring the speed of said walking or running using well known motion analysis systems like a treadmill, a Vicon® or CODA® camera system, a speedometer, measurements by a GPS receiver carried by the person, or a known distance and time taken to travel that distance. The last method, viz. using a known time and distance may be preferred for an individual having no access to advanced motion analysis systems. For this purpose a device suitable for the method may comprise functionalities such as the possibility to measure time and to store a distance. Since the correlation is found to be stable, it may be satisfactory to determine such a correlation only once for a given product. However, it is acknowledged that individual calibration may result in higher accuracy.

Some of the steps can be performed in a different order, provided that deducing the speed of the human from the correlation is the final step, viz. that this step (7) is performed after all the other steps. It is evident that the sensor has to placed before both the step of determining a COP gait line and calculating the COP speed from the gait line, and the step of determining whether the person is walking or running. So, one may first obtain a correlation (6) (master curve) between the speed of a person and a COP speed. As a second step one may provide a pressure sensor (10) between the sole of the foot and a surface. After which second step a centre of pressure gait line is determined, the centre of pressure speed is calculated (4) from the gait line, and it is detected (5) whether the person is walking or running. In another embodiment of the method, the correlation between the COP speed and the walking or running speed is determined afterwards, viz. after the COP speed has been determined. Of course this embodiment does not allow providing information about the speed of the person in real-time. It can only be used for analysis.

After having deduced the speed of the person, one can calculate the distance the person has been walking and running. If one knows the total distance that has to be run or walked, one can or course also determine the time or distance still to go. In general the speed of a person will not be constant all the time, but this can be taken into account by integrating the speed in time or by sampling the speed at sufficient high frequency. Similarly it is possible to forecast the time it will take the person to arrive at a predetermined location.

Many of the steps as described above can be embodied in a software product with a program of instructions for making a programmable processing unit perform the derivation of the speed, the software product being either a tangible product, for example a DVD, or intangible, for example via internet.

Such a software product may in particular be suited to make the programmable processing unit perform the steps of
  determining a centre of pressure gait line (3) and calculating a centre of pressure speed (4) from the gait line, and
  deducing the speed (7) of the person from the correlation (6) between the speed of a walking or running person and the centre of pressure speed.

The software product may be suited for obtaining the correlation (6) (e.g. master curve) between the speed of a walking or running person and the centre of pressure speed as described elsewhere in this document. The software product may even or in addition be suited for detecting whether the person is walking or running and/or for calculating distance and/or time.

Example

A Vicon® motion analysis system was used to capture the motion of an athlete performing various gait styles and speeds along a runway instrumented with a piezoelectric crystal force plate. The centre of pressure position calculated from the force plate data was plotted against corresponding centre of mass position calculated from Vicon® data (assumed to be centre of the pelvis). The data showed that the centre of pressure speed did correlate with centre of mass speed for a period of time during a step at a variety of running speeds.

The experiment monitored eight persons continuously on a treadmill at a range of walking and running speeds using a pressure insole based system. The insole comprised eight sensors configured as shown in FIG. 3. This system comprised a capacitive pressure sensing insole from Zephyr Technologies, a processor and wireless transmitter electronic unit and a receiver and data acquisition unit. The persons were asked to walk for one minute at each increasing treadmill speed, from 4.5 km/h with 1.5 km/h increments through to 9 km/h, until the speed was such that they naturally had to begin running. After each minute of walking the participant was allowed to rest until they were ready to walk again.

From 10 km/h upwards speed was increased by increments of 1 km/h until the speed on the treadmill was such that the participant began to have difficulty keeping pace. The speed at which the participant first began to use a running gait was recorded. Each person ran for between 30 and 60 seconds at each treadmill speed. The moment at which the COP moves forward from the start point towards the end point was defined as the start time. The time taken for the COP to move from this moment to the moment at which the COP reaches the end point was used as the total displacement time. During one test of between 30 and 60 seconds many steps were taken by each participant. In each case the first ten steps and last ten steps were not considered for calculation due to the effects of familiarization with the treadmill speed, choice of gait and accelerations and decelerations occurring during these periods. The remaining steps were considered to be performed in a relatively steady state.

The COP velocity calculated from the insole pressure measurement was plotted against treadmill speed for each of the participants.

Figure 4:
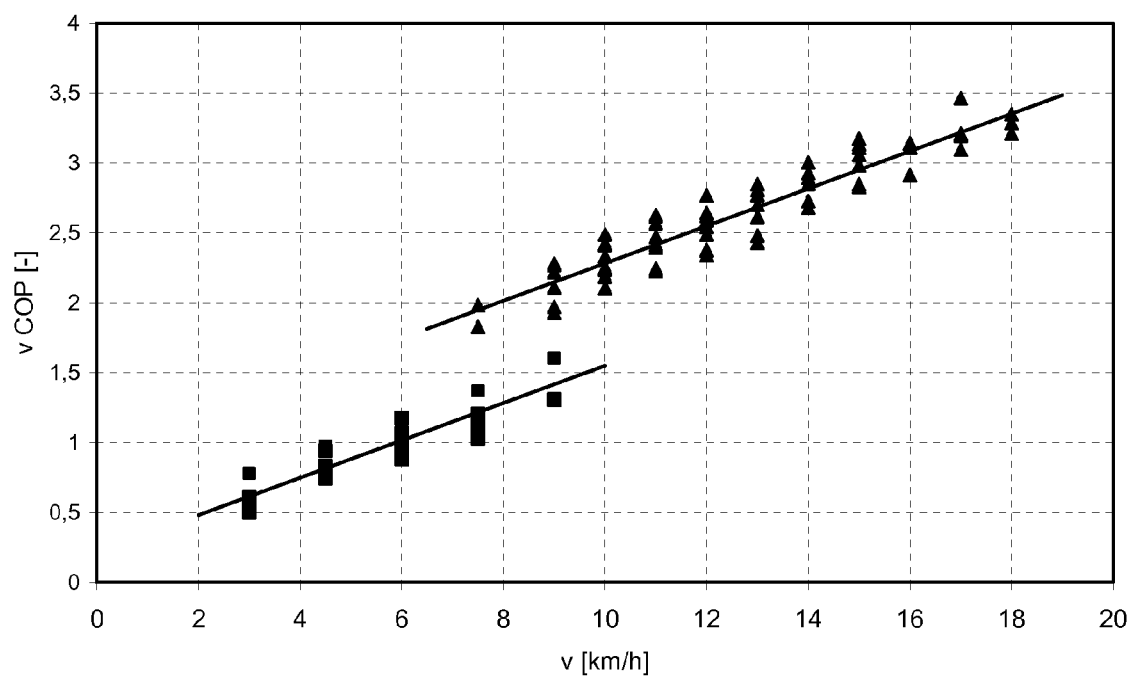
FIG. 4 shows an example of a correlation graph for walking and running for eight different persons.

FIG. 4 shows a graph of the running data displaying a clear correlation between COP and the treadmill speed even for this group of eight different people.

During the test the persons also walked at the slower speeds, only beginning to run when they felt the speed was sufficient to run comfortably. FIG. 3 shows a graph of the results including the treadmill speed for walking gaits. In this graph two separate correlations can be observed one for the walking gaits and another for the running gaits. Three persons were asked to run at speeds at which they had previously walked. FIG. 3 shows how the relationship holds for a running gait even at very low speeds more commonly associated with walking.

An experiment with a person running on a track also showed a systematic relation between COP speed and running speed. Without limitation to the invention one could theorize by hindsight that the relationship between the COP speed and running speed could be explained because the change of COP position is related to the change of the position of the person's centre of mass (COM, usually located in the torso) relative to the supporting foot. Initially, when the foot first touches the ground during walking or running, the foot is forward of the COM. Finally, when the foot is lifted from the ground during walking or running, the foot is backward of the COM. During all this time the COM moves forward. Between these time points, there is a time interval in which the COP also moves forward. Near the first touch and lift off there may be different movement, dependent on running style, stride length, cadence (step frequency) etc. These movements may not have a consistent relation to COM movement, but at least in the core time interval of forward COP movement there is a consistent relation between COP movement and COM movement, although of course the COP velocity is lower than COM velocity, because the COP moves within the foot area, which remains at a substantially fixed position, whereas the COM moves relative to the foot area over a distance permitted by the height of the COM above the foot.

The COM motion during COP motion occurs for walking and running under any circumstances, whether on a treadmill or on the road. In this way the correlation between the person's speed and COP speed arises. The experiments confirm that at least on average this results in a consistent relation between computed COP speed and centre of mass speed. The relation for walking is different from that of running, because during walking part of the time both feet are on the ground so that the force exerted with one foot can affect the position of the COP of the other foot.

Of course, unusual body motion during an individual step can have the effect that the COP speed in that individual step does not result in an accurate determination of the speed of the person (a step being defined as the time interval during which the foot for which the COP speed is determined is on the ground). But for most steps an accurate determination of speed of the person will result. In an embodiment, the effect of inaccuracy for individual steps may be reduced by combining the COP speed determined for a plurality of steps, e.g. by averaging or by taking a median value of the COP speed of the plurality of steps and using the combined value to look up the speed of the person using the correlation. Alternatively the COP speed determined for the plurality of steps may combined by using the COP speed for the individual steps to look up the person's speed values and by combining these person's speed values e.g. by averaging or by taking a median value.

The final step in determining the speed of the human is to correlate the measured centre of pressure velocity to the speed (i.e. for example to translate the COP velocity into speed) by using the master curve. Preferably this is done automatically by a processing unit, but the speed can also be determined by hand by obtaining the speed from a printed or displayed master curve.

Figure 5:
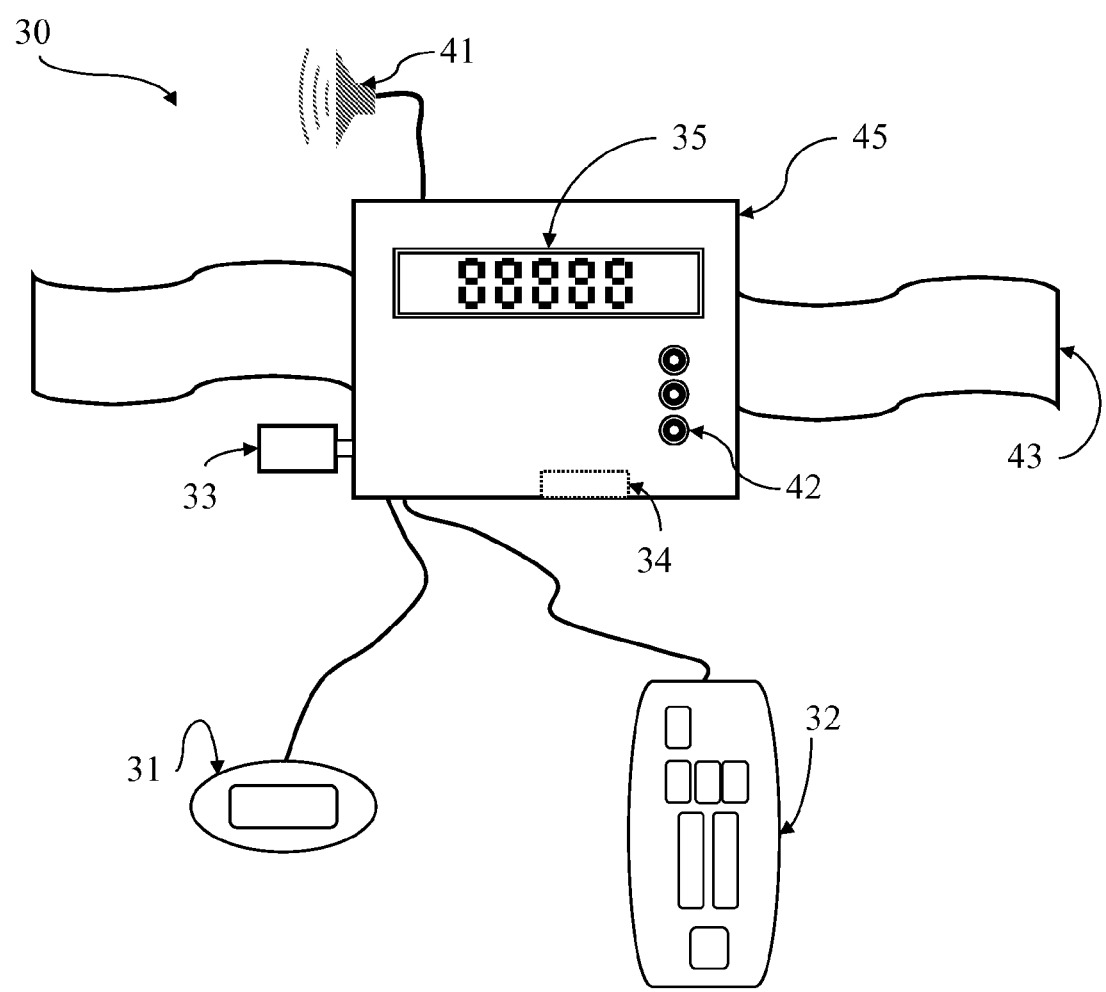
FIG. 5 shows a schematic representation of a system for determining the speed of a walking or running person.

All the embodiments of the method, whether discussed above or not, can be implemented in a system for providing the speed of a walking or running person. The inventors found of particular interest the system in which the user, more in particular the running or walking person, is informed during his activity about his speed. An exemplary embodiment of the system is shown in FIG. 5. This embodiment of the system (30) comprises a sensor (31) for sensing whether a first foot of the person is in contact with a supporting surface and a pressure sensor (32) for determining the centre of pressure of the second foot, which sensor is suitable for placing in a shoe. As was mentioned before in the description of the method, such sensors have particular advantages and are very well suited for determining the gait line and subsequently the centre of pressure speed. In a specific embodiment both sensors (31,32) are pressure sensors suited for determining a gait line. The system further comprises a memory (33) for storing the correlation between the speed of a walking or running person and the centre of pressure speed. This memory can be programmed with the proper data in advance, more in particular by the provider of the system, or the data can be stored in the memory by the user, as will described below.

The system further comprises a processing unit (34) for calculating a centre of pressure speed out of the measured pressure data. A proper human interface (35), for example a display, presents the information of the speed to the user. This user interface, however, may also be or comprise a loudspeaker like for example a headphone (41). Acoustic presentation may be preferred because reading during running is more troublesome than listening. For the acoustic presentation the system may comprise an electronic voice unit for transforming the calculated speed to a text in a human language. If the user is not interested in an accurate value of the speed the optical presentation may be in the form of for example a number of light emitting diodes (LEDs), the number of lighting LEDs being indicative for the speed. In a similar way the acoustic presentation may be in the form of sound pulses of which the frequency increases with the speed.

As mentioned before, the correlation data may be stored in the memory by the provider of the system, either permanently, for example on a digital recording device, or temporary. The correlation data may even be provided wirelessly or via internet. However, the system may also be configured for programming by the user. For this purpose the system will comprise for example keys (42) or voice recording means to allow the user to introduce data into the memory or the processing unit and otherwise instruct the system. The user may for example introduce a known distance from which the processing unit calculates the speed. By repeating this procedure for different running and walking speeds, the user can make his own master curve for the relationship between the centre of mass speed and the centre of pressure speed.

Further, the processing unit and human interface can be configured to calculate and present the distance that has been run or walked or, when for example the total distance has been introduced, the distance still to go.

The memory, processing unit and human interface can be incorporated in one apparatus (45) that can be attached to the person by for example a belt or an armband (43). This apparatus may comprise a battery for power supply or for example solar cells.

Summarizing, an embodiment of the invention provides a method of determining the speed of a walking or running person from foot motion, using at least one pressure sensor between a first foot of the person and a support surface, and further using a correlation (6) between the speed of walking or running and the centre of pressure speed, the method comprising determining a centre of pressure gait line (3) and calculating a centre of pressure speed (4) from the gait line, deriving the speed (7) of the person from the centre of pressure speed (4) and the correlation between the centre of pressure speed.

The centre of pressure gait line may be a series of computed positions of the centre of pressure, e.g. a weighted average of positions on the foot or shoe sole with weights in proportion to respective pressures measured at these positions. In a further embodiment the method further comprises detecting whether the person is walking or running (5), deriving the speed (7) of the person from the centre of pressure speed (4) and the correlation between the centre of pressure speed and the speed of the one of walking or running of the person that has been detected.

In each of these embodiments, the centre of pressure speed (4) may be calculated for example displacement of the centre of pressure in a time interval from a first time point at which centre of pressure speed (4) in a forward direction of the foot starts to exceed a first threshold and a second time point at which centre of pressure speed (4) in a forward direction of the foot ceased to exceed a second threshold. The first and second threshold may be zero, so that the first and second time points may be start and end time points of forward COP motion. The centre of pressure speed (4) may also be calculated from a coefficient of a function that is fitted to the centre of pressure as a function of time for example. A computer program product comprising a program of instructions for a programmable computer may be provided that, when executed by the computer will cause the computer to perform the steps of the method.

The derived speed may be used for generating a signal indicating the speed to a user via a human user interface for example (e.g. on a display). In a further embodiment, only a correlation between one of the speed of walking or running is provided (e.g. only for running) and the speed is derived (or used to generate the signal) using the correlation only if that one of walking and running is detected.

In another further embodiment, a first correlation between the speed of walking and the centre of pressure speed and a second correlation between the speed of walking and the centre of pressure speed are provided and the speed (7) of the person is derived using the first correlation if it has been detected that the person is walking and using the second correlation if it has been detected that the person is running.

The detection whether the person is walking or running (5) may be performed for example by detecting whether there are time intervals when the person has both feet on the ground or not respectively. The correlation may be provided for example a stored data representing a master curve that relates the speed of walking or running of the person and the centre of pressure speed. In an embodiment the method comprises obtaining the correlation by using a predetermined correlation. In another embodiment the method comprises a calibration phase with a step of obtaining the correlation by determining the centre of pressure speed (4) of a person during the calibration phase (e.g. the person for which the correlation will be used later to derive the speed of walking or running, or a different person) and measuring the speed of that person during the calibration phase.

In an embodiment a combination of the centre of pressure speed determined for a plurality of steps (time intervals wherein the foot is on the ground, e.g. over three or more steps) may used to determine the speed of the person using the correlation. In this way the effect of disturbances of individual steps can be reduced.

Furthermore, an embodiment provides for a system (30) for determining the speed of a walking or running person, the system comprising a pressure sensor (32) for measuring pressures to determine the centre of pressure of a first foot of the person;

a memory (33) for storing a correlation between the speed of a walking or running person and the centre of pressure speed, a processing unit (34) configured to calculate a centre of pressure speed from sensing result of the pressure sensor (32) and to derive the speed of the walking or running person from the calculated centre of pressure speed and the correlation. The processing system may configured to execute any one or more of the described embodiments of the method. As used herein, "configured to" means that the processing unit (34) has a program that will make it to perform the action that it is configured to perform, or that it has circuitry that will make it do so, or a mix of both. The processing unit may comprise one or a plurality of processors to perform the function. In a further embodiment the processing unit may be configured to compute the speed from a combination of the centre of pressure speeds determined for a plurality of steps. The system may comprise a shoe on or in which the pressure sensor (32) is provided.

In a further embodiment the system may comprise a human interface, such as a display or audio output for presenting the derived speed (35). In a further embodiment the system may comprise a further sensor (31) for sensing whether a second foot of the person is in contact with a supporting surface. The processing unit (34) may be configured to detect whether the person is walking or running dependent on the output of the further sensor (31), for example dependent on whether there are time intervals when the person has both feet on the ground or not respectively (as shown by the output of the further sensor and the pressure sensed by the pressure sensor (32).

In a further embodiment, only a correlation between one of the speed of walking or running is provided (e.g. only for running) and the speed is derived (or used to generate the signal) using the correlation only if that one of walking and running is detected. In another further embodiment, a first correlation between the speed of walking and the centre of pressure speed and a second correlation between the speed of walking and the centre of pressure speed are provided and the speed (7) of the person is derived using the first correlation if it has been detected that the person is walking and using the second correlation if it has been detected that the person is running.

The invention claimed is:

1. A method of determining the speed of a walking or running person from foot motion comprising the steps of:

providing at least one pressure sensor between a first foot of the person and a support surface so as to determine the centre of pressure, the pressure sensor being configured for transmitting pressure data to a processing unit, determining a centre of pressure gait line and calculating a centre of pressure speed from the gait line, detecting whether the person is walking or running, obtaining a correlation between the speed of a walking or running person and the centre of pressure speed, and determining the speed of the person from the correlation.

2. The method according to claim 1 wherein the first step comprises providing an additional sensor between a second foot of the person and the support surface for detecting contact between the second foot and the support surface and wherein the step of detecting whether the person is walking or running is performed by comparing the signal of the pressure sensor and the signal of the additional sensor to detect whether both feet are lifted from the support surface simultaneously.

3. The method according to claim 2 wherein the additional sensor is configured for determining a centre of pressure of the second foot.

4. The method according to claim 1 wherein the pressure sensor is a capacitance based sensor.

5. The method according to claim 1 wherein the processing unit is attached to the person.

6. The method according to claim 1 further comprising determining at least one of a distance or an estimated time of arrival.

7. The method according to claim 1 wherein the step of determining a centre of pressure speed from the gait line comprises determining a start time, at which the centre of pressure starts moving in a forward direction of the foot from a time of contact with the ground and an end time end time after which the centre of pressure does not move anymore in the forward direction, the centre of pressure speed being calculated from a quotient of a distance between centre of pressure positions at the end time and the start time and an elapsed time between the start time and the end time.

8. The method according to claim 1 wherein the steps of
determining a centre of pressure gait line and calculating a centre of pressure speed from the gait line, and
determining the speed of the person from the correlation are executed using a software product operatively associated with the processor.

9. The method according to claim 1 wherein the step of obtaining a correlation between the speed of a walking or running person and the centre of pressure speed is executed using a software product operatively associated with the processor.

10. A system for providing the speed of a walking or running person comprising:

a sensor for sensing whether a first foot of the person is in contact with a supporting surface, a pressure sensor for determining a centre of pressure of a second foot and for determining a centre of pressure gait line, which sensor is suitable for placing in a shoe, a memory for storing a correlation between a speed of a walking or running person and a centre of pressure speed, a processing unit for calculating the centre of pressure speed from the gait line and, using the stored correlation, calculating a walking or running speed, and a human interface for presenting the walking or running speed.

11. The system according to claim 10, wherein the processing unit is configured to use the sensor and the pressure sensor to determine whether the person is walking or running, and use the correlation for a walking person or for a running person dependent on whether the person is determined to be walking or running.

12. The system according to claim 10, wherein the human interface comprises a display or a loudspeaker.

13. The system according to claim 10, wherein the human interface is suited for receiving a manual or an acoustic input for programming the processor unit or for storing data in the memory.

14. The method according to claim 1, wherein the at least one pressure sensor is configured to measure the pressure at a plurality of different locations on the first foot and to transmit pressure data to the communication unit, the step of determining the centre of pressure gait line comprising computing centre of pressure points for successive time points, each determined by weighting the different locations so as to resolve all forces into one point.

15. The method of claim 1, further comprising:
determining a first time point at which the centre of pressure location starts moving in a forward direction of the first foot,
determining a second time point after which the centre of pressure location does not move anymore in the forward direction, and
determining the centre of pressure speed from the first time point and the second time point.

16. The method of claim 1, further comprising:
computing the centre of pressure speed from a fitted linear relationship between the centre of pressure location and a time.

17. The method of claim 1, further comprising:
selecting a first time point at which an instantaneous centre of pressure speed in a forward direction of the first foot starts to exceed a threshold value that is larger than zero, and
determining the centre of pressure speed from a change of centre of pressure positions after the first time point.

* * * * *